US008904872B2

(12) United States Patent
Langlois et al.

(10) Patent No.: US 8,904,872 B2
(45) Date of Patent: *Dec. 9, 2014

(54) DETECTION OF CHANNEL SATURATION IN PHASE-ARRAY ULTRASONIC NON-DESTRUCTIVE TESTING

(75) Inventors: Pierre Langlois, Stoneham (CA); Michael Drummy, North Reading, MA (US)

(73) Assignee: Olympus NDT, Waltham, MA (US)

( * ) Notice: Subject to any disclaimer, the term of this patent is extended or adjusted under 35 U.S.C. 154(b) by 973 days.

This patent is subject to a terminal disclaimer.

(21) Appl. No.: 12/981,228

(22) Filed: Dec. 29, 2010

(65) Prior Publication Data

US 2011/0100089 A1 May 5, 2011

Related U.S. Application Data

(62) Division of application No. 11/354,221, filed on Feb. 14, 2006, now Pat. No. 7,958,769.

(60) Provisional application No. 60/651,983, filed on Feb. 14, 2005.

(51) Int. Cl.
*G01N 29/26* (2006.01)
*G01N 29/44* (2006.01)
*G01N 29/04* (2006.01)
*G01N 29/06* (2006.01)
*G10K 11/34* (2006.01)

(52) U.S. Cl.
CPC .......... *G01N 29/262* (2013.01); *G01N 29/0609* (2013.01); *G01N 29/0645* (2013.01); *G10K 11/346* (2013.01); *G01N 2291/02491* (2013.01); *G01N 2291/044* (2013.01); *G01N 2291/106* (2013.01)
USPC ................ 73/602; 73/628; 702/116

(58) Field of Classification Search
CPC .......... G01N 29/0609; G01N 29/0645; G01N 29/262; G01N 2291/02491; G01N 2291/044; G01N 2291/106; G10K 11/346
USPC .......... 73/1.82, 1.88, 602, 628; 702/103–104, 702/116
See application file for complete search history.

(56) References Cited

U.S. PATENT DOCUMENTS

| 3,706,925 | A | * | 12/1972 | Engelhardt | 363/26 |
|---|---|---|---|---|---|
| 4,070,638 | A | * | 1/1978 | Reeder | 333/150 |
| 4,211,949 | A | * | 7/1980 | Brisken et al. | 310/322 |
| 4,771,786 | A | * | 9/1988 | Iinuma | 73/602 X |
| 8,166,822 | B1 | * | 5/2012 | Urbano et al. | 73/602 |
| 8,371,151 | B2 | * | 2/2013 | Langlois et al. | 73/1.82 |
| 8,577,629 | B2 | * | 11/2013 | Simard et al. | 702/104 X |
| 2002/0111568 | A1 | * | 8/2002 | Bukshpan | |

* cited by examiner

*Primary Examiner* — Thomas P Noland
(74) *Attorney, Agent, or Firm* — Ostrolenk Faber LLP

(57) ABSTRACT

The present invention relates to a method of detecting non-linear operation of a measuring device comprising an array of transducers and at least one receiver channel portion. The method comprises receiving measured signals through transducers of the array, processing the measured signals from the transducers through the receiver channel portion, combining the processed measured signals to produce a combined measurement signal, and detecting non-linearity of the combined measurement signal and non-linear operation of the measuring device by detecting saturation of the receiver channel portion. In one embodiment, the receiver channel portion comprises an analog-to-digital converter, a threshold is assigned to a digital output of the analog-to-digital converter, and saturation of the receiver channel portion is detected when the digital output of the analog-to-digital converter oversteps the assigned threshold. In one application of the invention, the measuring device is a non-destructive testing device.

6 Claims, 3 Drawing Sheets

DETECTION OF CHANNEL SATURATION IN PHASE-ARRAY ULTRASONIC NON-DESTRUCTIVE TESTING

CROSS-REFERENCE TO RELATED APPLICATION

The present application is a Divisional of U.S. patent application Ser. No. 11/354,221, filed Feb. 14, 2006, the contents of which are incorporated herein by reference.

This application claims the benefit of U.S. Provisional Application No. 60/651,983, filed Feb. 14, 2005, the entire contents of which are incorporated by reference.

FIELD OF THE INVENTION

The present invention relates to the detection of non-linearity in a measuring apparatus.

BACKGROUND OF THE INVENTION

Generally speaking, linearity is an essential feature of an accurate measuring apparatus. More specifically, when a signal detected by a measuring apparatus is amplified by a certain gain, the amplified output signal must be proportional to the detected signal. If this proportionality is not respected and no correction is made, the resulting signal is likely to be erroneous and lead to wrongful interpretation.

In the area of non-destructive testing (NDT) of materials and structures, a so-called "phase array" ultrasonic technique uses n channels including, for example, an array of n ultrasonic transducers. The n ultrasonic transducers are excited according to a given focal law delay profile to ultrasonically scan the tested material or structure. Echoes from defects or flaws present in the tested material or structure are detected by the n ultrasonic transducers to produce corresponding separate channel signals. An average of the channel signals is calculated prior to processing thereof.

Those of ordinary skill in the art will appreciate that saturation of at least one of the n channels will cause non-linearity of the measuring apparatus. More specifically, the calculated average will be erroneous and not representative of the reality.

SUMMARY OF THE INVENTION

To overcome the above discussed problem, the present invention relates, according to a first aspect, to a method of detecting non-linear operation of a measuring device comprising an array of transducers and at least one receiver channel portion. This method comprises receiving measured signals through transducers of the array, processing the measured signals from the transducers through said at least one receiver channel portion, combining the processed measured signals to produce a combined measurement signal, and detecting non-linearity of the combined measurement signal and non-linear operation of the measuring device by detecting saturation of said at least one receiver channel portion.

According to a second aspect, the present invention relates to a method of detecting non-linear operation of a measuring device comprising an array of n transducers and a number of n receiver channel portions respectively associated to the n transducers. This method comprises receiving measured signals through the n transducers, processing the measured signals from the n transducers through the corresponding n receiver channel portions, combining the processed measured signals to produce a combined measurement signal, and detecting non-linearity of the combined measurement signal and non-linear operation of the measuring device by detecting saturation of at least one of the receiver channel portions.

According to a third aspect, the present invention relates to a method of detecting non-linear operation of a measuring device comprising an array of transducers and at least one receiver channel portion comprising an analog-to-digital converter. The method comprises assigning a threshold to a digital output of the analog-to-digital converter, receiving measured signals through transducers of the array, processing the measured signals from the transducers through said at least one receiver channel portion, and detecting non-linear operation of the measuring device by detecting saturation of said at least one receiver channel portion when the digital output of the analog-to-digital converter oversteps the assigned threshold.

According to a fourth aspect, the present invention relates to a method of detecting non-linear operation of a measuring device comprising an array of n transducers and a number of n receiver channel portions respectively associated to the n transducers and each comprising an analog-to-digital converter. This method comprises assigning a threshold to a digital output of the analog-to-digital converters, receiving measured signals through the n transducers, processing the measured signals from the n transducers through the n receiver channel portions, respectively, and detecting non-linear operation of the measuring device by detecting saturation of at least one of the receiver channel portions when the digital output of the corresponding analog-to-digital converter oversteps the assigned threshold.

According to a fifth aspect, the present invention relates to a method of non-destructive testing of a material or structure using an array of ultrasonic transducers, comprising generating signals supplied to ultrasonic transducers of the array to produce ultrasonic waves propagating through the material or structure, receiving echoes of the ultrasonic waves through ultrasonic transducers of the array to produce echo signals, processing the echo signals through at least one receiver channel portion and combining the processed echo signals to produce a combined measurement signal; and detecting non-linearity of the combined measurement signal by detecting saturation of said at least one receiver channel portion.

According to a sixth aspect, the present invention relates to a device for detecting non-linear operation of a measuring device comprising an array of transducers. This device comprises at least one receiver channel portion so configured as to receive measured signals through transducers of the array and to process the measured signals from the transducers, a combiner of the processed measured signals to produce a combined measurement signal, and a detector of saturation of said at least one receiver channel portion, detection of saturation of said at least one receiver portion indicating non-linearity of the combined measurement signal and non-linear operation of the measuring device.

According to a seventh aspect, the present invention relates to a device for detecting non-linear operation of a measuring device comprising an array of n transducers. This device comprises: a number of n receiver channel portions respectively associated to the n transducers, the n receiver channel portions being so configured as to receive measured signals through the n transducers, respectively, and to process the measured signals from the transducers; a combiner of the processed measured signals to produce a combined measurement signal; and a detector of saturation of at least one of the n receiver channel portions, detection of saturation of said at least one receiver channel portion indicating non-linearity of the combined measurement signal and non-linear operation of the measuring device.

According to an eighth aspect, the present invention relates to a device for detecting non-linear operation of a measuring device comprising an array of transducers. This device comprises: at least one receiver channel portion comprising an analog-to-digital converter, a threshold being assigned to a digital output of the analog-to-digital converter, and said at least one receiver channel portion being so configured as to receive measured signals through transducers of the array and to process the measured signals from the transducers; and a detector of saturation of said at least one receiver channel portion when the digital output of the analog-to-digital converter oversteps the assigned threshold, detection of saturation of said at least one receiver channel portion being indicative of non-linear operation of the measuring device.

According to a ninth aspect, the present invention relates to a device for detecting non-linear operation of a measuring device comprising an array of n transducers. This device comprises: a number of n receiver channel portions respectively associated to the n transducers and each comprising an analog-to-digital converter, wherein a threshold is assigned to a digital output of the analog-to-digital converter, and wherein said n receiver channel portions are so configured as to receive measured signals through the n transducers, respectively, and to process the measured signals from the transducers; and a detector of saturation of at least one of the receiver channel portions when the digital output of the analog-to-digital converter of said one receiver channel portion oversteps the assigned threshold, detection of saturation of said at least one receiver channel portion being indicative of non-linear operation of the measuring device.

According to a tenth aspect, the present invention relates to a device for non-destructive testing of a material or structure using an array of ultrasonic transducers, comprising: a plurality of channels connected to ultrasonic transducers of the array, said plurality of channels defining generators of signals supplied to the ultrasonic transducers to produce ultrasonic waves propagating through the material or structure; at least one receiver channel portion so configured as to receive echoes of said ultrasonic waves through ultrasonic transducers of the array to produce echo signals and to process the echo signals; a combiner of the processed echo signals to produce a combined measurement signal; and a detector of saturation of said at least one receiver channel portion, detection of saturation of said at least one receiver channel portion indicating non-linearity of the combined measurement signal.

The foregoing and other objects, advantages and features of the present invention will become more apparent upon reading of the following non-restrictive description of an illustrative embodiment thereof, given by way of example only with reference to the accompanying drawings.

DETAILED DESCRIPTION OF THE ILLUSTRATIVE EMBODIMENT

Figure 1:
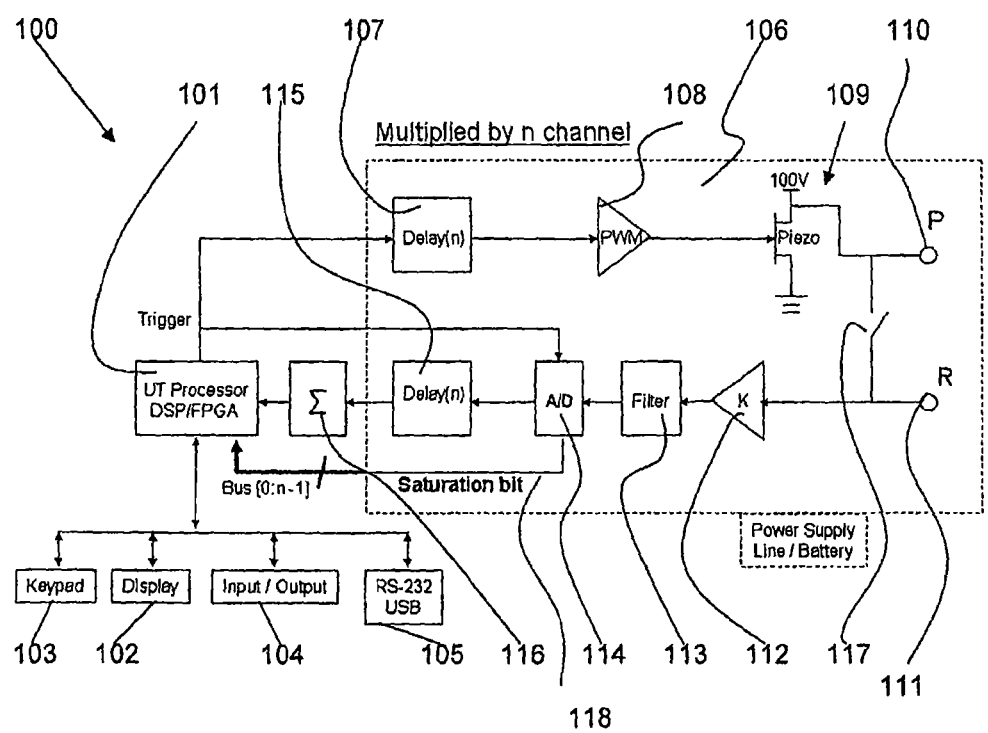
FIG. 1 is a schematic block diagram of a non-restrictive illustrative embodiment of a phase-array ultrasonic non-destructive testing apparatus using n channels.

FIG. 1 is a schematic block diagram of a non-limitative example of phase-array ultrasonic non-destructive testing apparatus 100. Although the present invention will be described in relation to a non-limitative example of phase-array ultrasonic non-destructive testing apparatus, it should be kept in mind that the present invention can also be used in connection with other types of measuring apparatuses.

As shown in FIG. 1, the phase-array ultrasonic non-destructive testing apparatus 100 comprises an ultrasonic processor 101 associated with a display unit 102, for example a LCD (Liquid Crystal Display) display, and a keypad 103, input/output peripherals and/or ports 104 and RS-232 USB port 105.

The ultrasonic processor 101 is responsible for system synchronization, signal processing and real-time displaying of the received echo signals.

More specifically, the ultrasonic processor 101 produces synchronized pulses with pre-programmed width. The synchronized pulses with pre-programmed width are processed through a number of n substantially identical and parallel channels such as 106 respectively associated to ultrasonic transducers (not shown), such as piezoelectric elements, of an ultrasonic phase-array probe (not shown). In one embodiment, the number n of channels 106 is equal to the number of ultrasonic transducers of the phase-array probe and each of the n channels 106 is associated to a respective single one of the n ultrasonic transducers for supplying and receiving signals to and from this transducer. According to an alternative, each channel 106 is associated to:
- a first ultrasonic transducer supplied with signals from the channel 106 to produce ultrasonic waves propagating through the material or structure to be investigated; and
- a second ultrasonic transducer to detect echoes produced by reflection of ultrasonic waves on boundaries, defects or flaws in the investigated material or structure and to produce corresponding echo signals supplied to the associated channel 106.

The synchronized pulses with pre-programmed width are supplied to a delay circuit 107 of each channel 106. The function of the delay circuit 107 is to delay the pulses from the ultrasonic processor 101 in order to supply to the corresponding ultrasonic transducer the pulses with a time delay corresponding to the delay associated to this transducer in a corresponding, pre-calculated focal law delay profile.

The delayed pulses from delay circuit 107 are processed through a pulse width modulator 108 for adjusting the width of the pulses as desired or required by the intended application, and then amplified by a high power pulse amplifier 109 prior to being supplied to the corresponding ultrasonic transducer connected to a pulser output 110 through, for example, an ultrasonic cable (not shown). The function of the ultrasonic transducer is to create ultrasonic waves propagating through the material or structure to be investigated.

Ultrasonic echoes produced by reflection of ultrasonic waves on boundaries, defects or flaws in the material or structure being investigated are detected by the ultrasonic transducer connected to the receiver input 111. As indicated in the foregoing description, the same ultrasonic transducer or different ultrasonic transducers can be connected to the output 110 and input 111. Depending on the configuration of the connections and the operation of the phase-array ultrasonic non-destructive testing apparatus 100, a switch 117 can be actuated to interconnect or disconnect the output 110 and input 111 as required. Switch 117 can be operated manually or through the ultrasonic processor 101 as required.

The reflected ultrasonic echoes are converted by the ultrasonic transducer into electrical echo signals that are processed by a receiver portion of the channel 106. In one embodiment, a receiver channel portion is provided for each channel 106. It is also within the scope of the present invention to provide only one receiver channel portion for all the channels 106 using for example a multiplexer (not shown) for successively connecting the transducers to a single receiver channel portion.

Referring back to FIG. 1, in a receiver channel portion, the echo signals from the ultrasonic transducer are amplified by an amplifier 112, filtered in accordance with techniques well known to those of ordinary skill in the art through a filter 113 to remove parasitic or unwanted signal components, and then digitized through an analog-to-digital (A/D) converter 114. The digitized echo signals from the analog-to-digital converter 114 are then delayed by a delay circuit 115 using the same focal law delay profile as applied by delay circuit 107. A combiner 116 combines, for example sums the digitized and delayed echo signals from all the channels 106 to form a sum that is processed through the DSP of the ultrasonic processor 101 to form an average that is stacked to form, for example, a S-Scan image displayed on the display unit 102 for interpretation by the operator. The display unit 102 can be a liquid crystal display (LCD) calibrated in units of time, depth or distance. A multi-color LCD display can also be used to provide interpretive assistance. Just a word to mention that an advantage of displaying the reflected, digitized, delayed, summed and processed echo signals under the form of a real-time S-Scan image display instead of only displaying A-Scan signals, is that the boundaries, flaws or defects and their positions can be more easily identified on the display unit 102. S-Scan images and A-Scan signal are well known to those of ordinary skill in the art and, for that reason, will not be further described in the present specification.

Finally the S-Scan images can be stored through the input/output port 104 or through the USB port 105. Internal data logging capabilities can also be provided for to record selected full waveforms and setup information associated with each test.

Figure 2:
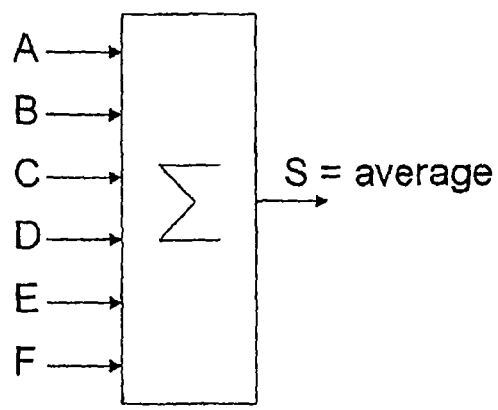
FIG. 2 is a schematic block diagram showing an example of averaging of the signals from six (6) different channels of the phase-array ultrasonic non-destructive testing apparatus.

As indicated in the foregoing description, should one of the n channels be saturated before the processor 101 calculates the average of the received ultrasonic channel signals, this average will be affected, that is erroneous and not representative of the reality. This situation can be illustrated in FIG. 2 through a non-limitative example including six (6) channels A, B, C, D, E and F (n=6). In the example of FIG. 2, the average S is calculated by the combiner 116/processor 101 using the following relation:

$$S=(A+B+C+D+E+F)/6$$

In the non-limitative example of FIG. 2, let's consider that the maximum receiver 111 input signal level is 100% in each channel n before reaching saturation of that channel. As indicated in the following Table 1, let's also determine an initial average adjusted to a value of 40% and a focal law delay profile imposing the following values A=5%, B=50%, C=65%, D=65%, E=50% and F=5%.

More specifically, Table 1 shows values of the average obtained with a constant increase of receiver 111 input signal level (shown in italic) by steps of the order of 5%. This is made by simply adding at each step an increase of 5% on each channel n in order to obtain an average with the same percentage as the receiver 111 input signal level increase.

TABLE 1

Variation of the average as a function of the increase in A/D output signal level of each channel

| Receiver 111 Input Signal Level (%) | A/D Output Signal Level for Each Channel (%) | | | | | | Average (%) |
|---|---|---|---|---|---|---|---|
| | A | B | C | D | E | F | |
| 0  | 5  | 50  | 65  | 65  | 50  | 5  | 40.00 |
| 5  | 10 | 55  | 70  | 70  | 55  | 10 | 45.00 |
| 10 | 15 | 60  | 75  | 75  | 60  | 15 | 50.00 |
| 15 | 20 | 65  | 80  | 80  | 65  | 20 | 55.00 |
| 20 | 25 | 70  | 85  | 85  | 70  | 25 | 60.00 |
| 25 | 30 | 75  | 90  | 90  | 75  | 30 | 65.00 |
| 30 | 35 | 80  | 95  | 95  | 80  | 35 | 70.00 |
| 35 | 40 | 85  | 100 | 100 | 85  | 40 | 75.00 |
| 40 | 45 | 90  | 100 | 100 | 90  | 45 | 78.33 |
| 45 | 50 | 95  | 100 | 100 | 95  | 50 | 81.67 |
| 50 | 55 | 100 | 100 | 100 | 100 | 55 | 85.00 |
| 55 | 60 | 100 | 100 | 100 | 100 | 60 | 86.67 |
| 60 | 65 | 100 | 100 | 100 | 100 | 65 | 88.33 |

Figure 3:
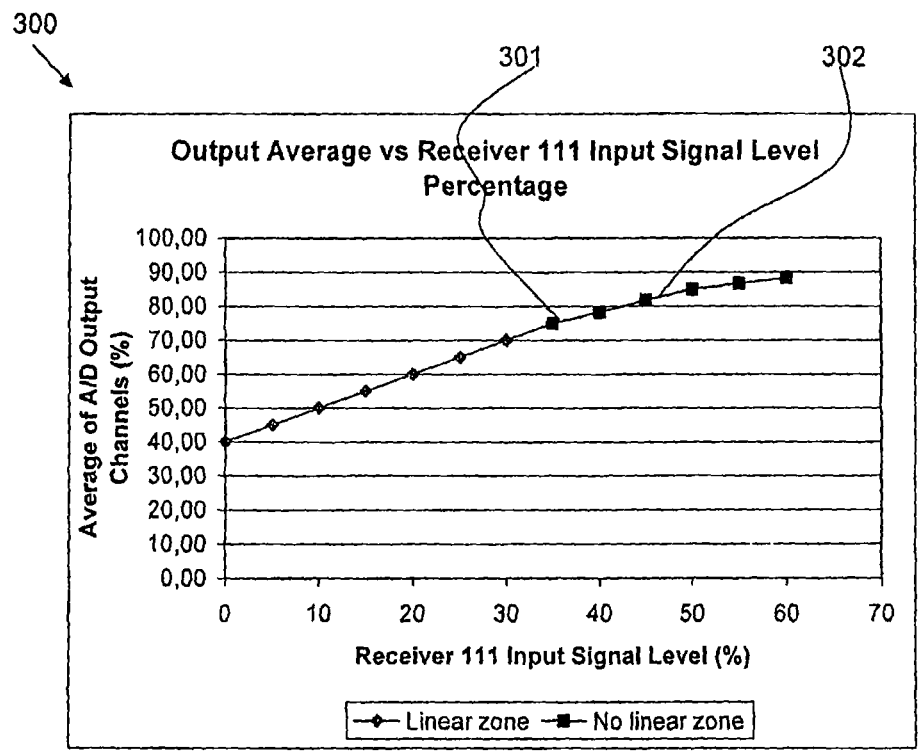
FIG. 3 is a graph showing the amplitude of an average of the six (6) A/D (analog-to-digital) output channels of FIG. 2 in relation to a percent increase of receiver input signal level.

The graph 300 of FIG. 3 shows that from point 301 of the curve, the calculated average is no longer proportional to the increase in receiver 111 input signal level (non-linear zone 302 in the graph of FIG. 3 and bold portion in Table 1). This situation is met as soon as one of the channels is saturated. This can be explained as follows: since every saturated channel n remains at the same A/D output level (100%) and the receiver 111 input signal level of the other channels n increases by 5%, variation of the average is no longer proportional to the increase in receiver 111 input signal level.

In the field of medical imaging, such a situation is not critical since saturation of one channel will result in an image deformation, for example a blurred image that can be visually detected on the display. The operator can then adjust the gain of the measuring apparatus in order to eliminate the image deformation.

In the case of NDT, it is very difficult, even impossible, for the operator to detect an irregularity, such as saturation of a channel, since the obtained results are not images but channel echo signals. This is the incentive for designing a phase-array ultrasonic non-destructive testing apparatus capable of producing an alarm indicating to the operator that at least one of the channels n is saturated.

Referring back to FIG. 1, the analog-to-digital converter 114 is designed to produce a saturation-indicative signal 118, for example a saturation bit, in response to detection of saturation of the corresponding channel n. This saturation bit 118 is supplied to the ultrasonic processor 101. In response to the saturation bit 118, the ultrasonic processor 101 produces an audible alarm and/or a visual alarm displayed on the unit 102 to indicate to the operator that at least one channel is saturated. The selection of an appropriate means for generating the alarm in response to the saturation bit 118 is believed to be within the capacity of those of ordinary skill in the art.

For example, the saturation-indicative signal 118 (ADx_OTR) can be simply a logic level 1 produced when the analog-to-digital converter 114 is saturated, i.e. when a bit overflow occurs during the analog-to-digital conversion.

According to a non-limitative alternative embodiment, saturation detection does not require the production of a saturation-indicative signal 118 nor a saturation threshold equivalent to the full scale conversion value of the analog-to-digital converter 114. More specifically, the alternative embodiment assigns as saturation threshold an output conversion value of the analog-to-digital converter 114 lower than the full scale conversion value, for example 1111111111 for a 10-bit analog-to-digital converter. For example, a threshold value of 1111111110 could be used.

According to this alternative embodiment, the digital output of the analog-to-digital converter 114 is monitored by a digital logic circuit (not shown) that detects the saturation and non-linearity event when the digital output of the analog-to-digital converter 114 oversteps the threshold value, for example "1111111110" in the above non-limitative example. This digital logic circuit (not shown) then produces an output signal representative of the detected saturation and non-linearity event of the phase-array ultrasonic non-destructive testing apparatus. When using a digital logic circuit according to the alternative embodiment, the ultrasonic processor 101 responds in the same way as described earlier in response to the saturation-indicative signal 118.

According to another non-limitative alternative embodiment, saturation detection does not require:
  a) the production of a saturation-indicative signal 118, nor
  b) a saturation threshold equivalent to the full scale conversion value of the analog-to-digital converter 114, nor
  c) the assignment of a saturation threshold to an output conversion value of the analog-to-digital converter 114, nor
  d) a digital logic output signal (not shown) resulting from detection of saturation event resulting from method c above.

Instead, when one of the stages within the entire signal path of the receiver channel portion, starting at input 111 and ending at the output of filter 113, becomes saturated, this event can be detected by the ultrasonic processor 101 by comparing the preceding measured echo signal level of each channel with the current measured echo signal level of each channel respectively. Specifically, the preceding and current measurements made for a particular channel are compared to determine whether the percent increase is the same as the percent increase calculated for any of the other channels with lower analog-to-digital converter 114 output values for the measured echo signals. If the percent increase is substantially lower than the other channels, then the ultrasonic processor 101 detects this condition and produces an output signal representative of the detected saturation and non-linearity event of the phase-array ultrasonic non-destructive testing apparatus.

In Table 1, the saturation and non-linearity condition is indicated by the bold numbers.

Non-limitative Example

The analog-to-digital converter 114 is a 10-bit analog-to-digital converter. The saturation-indicative signal 118 is initially equal to 0 (ADx_OTR=0). Since the analog-to-digital converter 114 is a 10-bit analog-to-digital converter, the maximum amplitude of the output digital signal is 1111111111. If the result of the analog-to-digital conversion is larger than 1111111111, bit overflow occurs and the saturation-indicative signal 118 is made equal to 1 (ADx_OTR=1). In response to ADx_OTR=1, a saturation alarm is generated by the ultrasonic processor 101 to indicate non-linear operation of the phase-array ultrasonic non-destructive testing apparatus.

Obviously, detection of the saturation is performed within each of the n channels 106, in order to ensure that no channel is saturated, or in the single receiver channel portion when a multiplexer as described hereinabove is provided.

Following the saturation alarm, the gain of the receiver channel portion(s) can be manually reduced by an operator or automatically reduced by the ultrasonic processor 101 in accordance with a predetermined protocol.

Although the present invention has been described in the foregoing description in connection with a non-restrictive illustrative embodiment thereof, numerous modifications to this non-restrictive illustrative embodiment can be implemented without departing from the scope and nature of the invention. For example, the present invention can be applied to measuring devices other than a phase-array ultrasonic non-destructive testing apparatus.

What is claimed is:

1. A method of non-destructive testing of a material or structure using an array of ultrasonic transducers, comprising:
  generating signals supplied to ultrasonic transducers of the array to produce ultrasonic waves propagating through the material or structure;
  receiving echoes of said ultrasonic waves through ultrasonic transducers of the array to produce echo signals;
  processing the echo signals through at least one receiver channel portion and combining the processed echo signals to produce a combined measurement signal;
  detecting non-linearity of the combined measurement signal by detecting saturation of said at least one receiver channel portion.

2. The method of claim 1, wherein said at least one receiver channel portion comprises a plurality of receiver channel portions.

3. A method according to claim 1, wherein detection of saturation of one of the receiver channel portions comprises:
  comparing a percent increase in said at least one of the receiver channel portions of a current echo signal with respect to a preceding echo signal, and the same percent increase in at least one other receiver channel portion processing an echo signal of lower amplitude, and
  detecting saturation when the percent increase in said one of the receiver channel portions is substantially lower than the percent increase in said at least one other receiver channel portion.

4. A device for non-destructive testing of a material or structure using an array of ultrasonic transducers, comprising:
  a plurality of channels connected to ultrasonic transducers of the array, said plurality of channels defining generators of signals supplied to the ultrasonic transducers to produce ultrasonic waves propagating through the material or structure;
  at least one receiver channel portion so configured as to receive echoes of said ultrasonic waves through ultrasonic transducers of the array to produce echo signals and to process the echo signals;
  a combiner of the processed echo signals to produce a combined measurement signal; and
  a detector of saturation of said at least one receiver channel portion, detection of saturation of said at least one receiver channel portion indicating non-linearity of the combined measurement signal.

5. The device of claim 4, wherein said at least one receiver channel portion comprises a plurality of receiver channel portions.

6. A device according to claim 4, wherein the detector of saturation of one of the receiver channel portions is so configured as to compare a percent increase in said at least one of the receiver channel portions of a current echo signal with respect to a preceding echo signal, and the same percent increase in at least one other receiver channel portion processing an echo signal of lower amplitude, and detect saturation when the percent increase in said one of the receiver channel portions is substantially lower than the percent increase in said at least one other receiver channel portion.

* * * * *